(12) United States Patent
Cui

(10) Patent No.: US 12,376,772 B2
(45) Date of Patent: Aug. 5, 2025

(54) DIABETES BIOSENSOR

(71) Applicant: Peking University, Beijing (CN)

(72) Inventor: Yue Cui, Beijing (CN)

( * ) Notice: Subject to any disclaimer, the term of this patent is extended or adjusted under 35 U.S.C. 154(b) by 63 days.

(21) Appl. No.: 18/539,336

(22) Filed: Dec. 14, 2023

(65) Prior Publication Data
US 2025/0194970 A1    Jun. 19, 2025

(30) Foreign Application Priority Data

Dec. 27, 2022    (CN) .................. 202211686888.X

(51) Int. Cl.
*A61B 5/1486*    (2006.01)
*A61B 5/00*      (2006.01)
*A61B 5/145*     (2006.01)

(52) U.S. Cl.
CPC ........ *A61B 5/1486* (2013.01); *A61B 5/14532* (2013.01); *A61B 5/4839* (2013.01); *A61B 2562/125* (2013.01)

(58) Field of Classification Search
CPC . A61B 5/1486; A61B 5/14532; A61B 5/4839; A61B 2562/125; A61M 37/0015
See application file for complete search history.

(56) References Cited

U.S. PATENT DOCUMENTS

| | | | | |
|---|---|---|---|---|
| 7,344,499 B1* | 3/2008 | Prausnitz | ......... | A61B 5/150022 |
| | | | | 600/347 |
| 2005/0070768 A1* | 3/2005 | Zhu | ................... | A61B 5/14532 |
| | | | | 600/309 |
| 2007/0227907 A1* | 10/2007 | Shah | ...................... | C25D 5/623 |
| | | | | 204/403.01 |
| 2010/0230285 A1* | 9/2010 | Hoss | .................. | A61B 5/14532 |
| | | | | 600/347 |
| 2014/0107450 A1* | 4/2014 | Simpson | ............ | A61B 5/14865 |
| | | | | 600/365 |

FOREIGN PATENT DOCUMENTS

| CN | 113171090 A | 7/2021 |
|---|---|---|
| CN | 115266865 A | 11/2022 |

* cited by examiner

*Primary Examiner* — Eric J Messersmith
*Assistant Examiner* — Kyle W. Kretzer

(57) ABSTRACT

The present invention provides a diabetes biosensor including a porous polymer membrane; two sides of the porous polymer membrane are provided with impermeable membranes; the impermeable membrane on one side is provided with a first electrode, the impermeable membrane on the other side is provided with a second electrode. Specific glucose oxidase is immobilized on the first electrode. In the present invention, the porous polymer membrane has the feature of multiple pores to facilitate the penetration of water and other liquids, and the impermeable membranes on two sides of the porous polymer membrane have the feature of impermeable; the porous polymer membrane, the impermeable membranes, the first electrode, and the second electrode together constitute a sandwich sensor; glucose generates hydrogen peroxide under the action of glucose oxidase; after the hydrogen peroxide generates electron gain and loss on the electrode, an electric signal change is generated and detected by the biosensor; and the biosensor can rapidly measure the blood glucose concentration. In addition, the biosensor can be used as a device for storing drugs, which facilitates the use of the biosensor to inject insulin into a patient with a high blood glucose concentration to control the blood glucose level.

9 Claims, 10 Drawing Sheets

Fabricate a first electrode and a second electrode on the surface of the impermeable membrane using a micro/nanofabrication method or a screen printing method, followed by drying

↓

Prepare a porous polymer membrane using a spin-coating method or a dip-coating method, followed by drying

↓

Spin-coat another layer of impermeable membrane polymer liquid, followed by drying

↓

Immobilize a mixture of an enzyme layer and an immobilization agent on the surface of the first electrode

↓

Immobilize an enzyme protective layer on the surface of the enzyme layer

FIG. 7

DIABETES BIOSENSOR

TECHNICAL FIELD

The present invention relates to the field of biosensors, and in particular to a diabetes biosensor.

BACKGROUND ART

Biomarkers are important diagnostic indicators of various diseases, which can reflect the metabolic status and the degree of damage of the human body, and provide reference for treatment. Meanwhile, with the change in people's lifestyle and dietary habits, the incidence of diabetes in China is also rising. According to the latest literature, the incidence of diabetes in China has reached 15.6%. Blood glucose monitoring has also become a more common item in biochemical monitoring, and the premise of blood glucose control is to accurately detect the blood glucose level, so it is particularly important to select appropriate blood glucose detection instruments and methods.

Biosensors are composed of two main parts, that is, a biological recognition element and a signal converter. The biological recognition element refers to a biologically active substance, such as an enzyme, an antigen, an antibody, a nucleic acid, a cell, a tissue, and the like, which has a molecular recognition ability and can specifically react with a substance to be detected. The main function of the signal converter is to convert the biological recognition into a detectable signal. At present, several methods are commonly used, such as electrochemical, optical, thermal, and mass analysis. The electrochemical method is one of the most ideal detection methods.

Methods of blood glucose monitoring are also constantly being improved. At present, the main blood glucose monitoring methods include a blood glucose meter for rapid detection and a biochemical analyzer. Fully automatic biochemical analyzers are mainly used to detect blood glucose in hospitals. However, these existing blood glucose detectors have the disadvantages of low sensitivity and inability to inject liquid medicine.

SUMMARY OF THE INVENTION

Aiming at the problems existing in the prior art, the present invention provides a diabetes biosensor, which can continuously and dynamically monitor the blood glucose concentration, and automatically adjust the injection amount of insulin in real-time according to the blood glucose concentration, to stabilize the blood glucose concentration in diabetic patients.

To achieve the above object, the present invention is achieved by the following technical solutions.

A diabetes biosensor includes a porous polymer membrane, and two sides of the porous polymer membrane are provided with impermeable membranes; the impermeable membrane on one side is provided with a first electrode, and the impermeable membrane on the other side is provided with a second electrode; and surfaces of the first electrode and the second electrode are provided with enzyme layers, and surfaces of the enzyme layers are provided with enzyme protective layers.

Preferably, the porous polymer membrane is made of a mesoporous polymer; the mesoporous polymer is a mixture of polyglycidyl methacrylate and polyethylene glycol, or polyvinyl alcohol.

Preferably, the impermeable membrane is selected from a commercial membrane or self-made.

When the impermeable membrane is selected from the commercial membrane, the porous polymer membrane is prepared by a spin-coating method or a dip-coating method on a commercial membrane substrate, and the impermeable membrane is attached to the other side of the porous polymer membrane before drying.

When the impermeable membrane is a self-made membrane, a first layer of impermeable membrane is formed by spin-coating a polymer aqueous solution for preparing the impermeable membrane, followed by drying; and then another layer of impermeable membrane polymer liquid is spin-coated, followed by drying, and then an enzyme layer setting process is performed.

A method for preparing the enzyme layer and an enzyme protective layer is as follows: dropping the enzyme layer and the enzyme protective layer liquid on an electrode to cover an integral electrode, or spin-coating the enzyme layer and the enzyme protective layer liquid to cover the integral electrode, or printing the enzyme layer and the enzyme protective layer liquid on parts or the whole of the electrode.

Preferably, a length of the porous polymer membrane is 0.5 mm to 15 mm, a width of the porous polymer membrane is 100 μm to 2 mm, and a thickness of the porous polymer membrane is 100 μm to 1 mm.

Preferably, the impermeable membrane is made of Teflon, polypropylene, polyethylene, polyvinyl chloride, polyethylene terephthalate, polycarbonate, polyurethane, thermoplastic polyurethane, polyimide, glass fiber, silk fibroin, chitosan, polylactic acid, silica gel, rubber, latex, thermoplastic elastomer, or perfluoro ethylene-propylene copolymer.

Preferably, the first electrode is a working electrode, the second electrode is a reference electrode/counter electrode, and the first electrode and the second electrode together form a two-electrode system.

The two-electrode system is fabricated using a micro/nanofabrication method or a screen printing method;

The micro/nanofabrication method of the two-electrode system is as follows:
  (1) working electrode: evaporation or sputtering of the micro/nanofabrication method is used to obtain a nanolayer of gold or platinum before electroplating thereon to produce a Prussian Blue (PB) layer to obtain a gold/PB electrode or a platinum/PB electrode; and
  (2) reference electrode/counter electrode: a silver electrode is produced through sputtering or evaporation, and then part of the silver in a ferric chloride solution generates silver chloride through a chemical reaction to obtain a silver/silver chloride electrode.

The screen-printing method of the two-electrode system is as follows:
  (1) working electrode: a gold composite paste, a platinum composite paste, or a carbon composite paste is screen printed; and
  (2) reference electrode/counter electrode: a silver/silver chloride composite paste is screen printed.

Preferably, the first electrode is made of a carbon composite material, or a gold composite material, or a platinum composite material, and the second electrode is made of silver/silver chloride.

Preferably, the enzyme layer is immobilized on the surface of the first electrode with an immobilization agent, and the immobilization agent is glutaraldehyde, chitosan, or Nafion.

The enzyme protective layer is a polymer composite material or a multi-layer material, and the polymer composite material is one or more of polyvinyl alcohol, polyethylene glycol, and polyurethane.

Preferably, the enzyme layer is directly added to the surface of the first electrode.

An immobilization agent layer is provided between the enzyme protective layer and the enzyme layer, the enzyme protective layer is a multi-layer material, and the multi-layer material is one or more of glutaraldehyde, polyvinyl alcohol, polyethylene glycol, and polyurethane.

The advantageous effects of the present invention are as follows:

The porous polymer membrane has the feature of multiple pores to facilitate the penetration of drug liquid, and the impermeable membranes on two sides of the porous polymer membrane have the feature of impermeable; the porous polymer membrane, the impermeable membrane, the first electrode, and the second electrode together constitute a sandwich sensor capable of detecting the glucose concentration in the subcutaneous tissue liquid, so that the glucose generates hydrogen peroxide under the action of glucose oxidase. When a constant voltage is applied to the working electrode (concerning the reference electrode/counter electrode), hydrogen peroxide generates electrons gain and loss on the working electrode, and then a current signal change is generated and detected by the circuit board or chip, thereby enabling the biosensor to perform rapid and continuous measurement of blood glucose concentration. In addition, the biosensor can be used as a device for storing drugs, which facilitates the use of the biosensor to inject insulin into a patient with a high blood glucose concentration to control the blood glucose level.

BRIEF DESCRIPTION OF DRAWINGS

FIG. 7 is a flowchart of embodiment 6 of the present invention;

Figure 1:
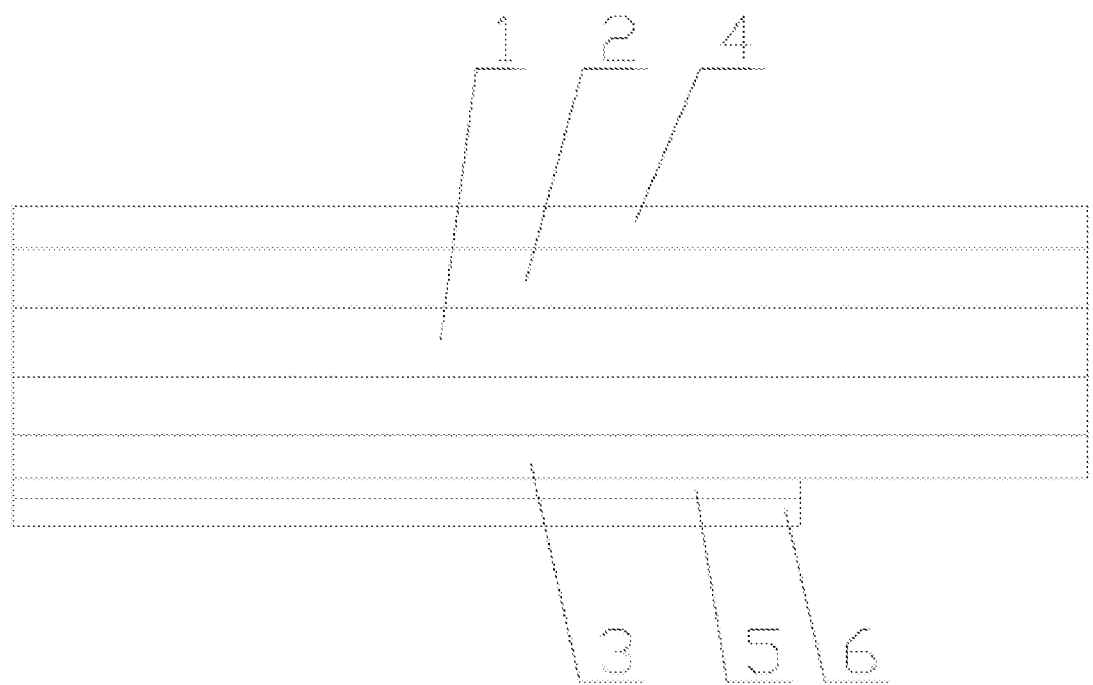
FIG. 1 is an overall structural diagram of embodiment 1 of the present invention.
Figure 2:
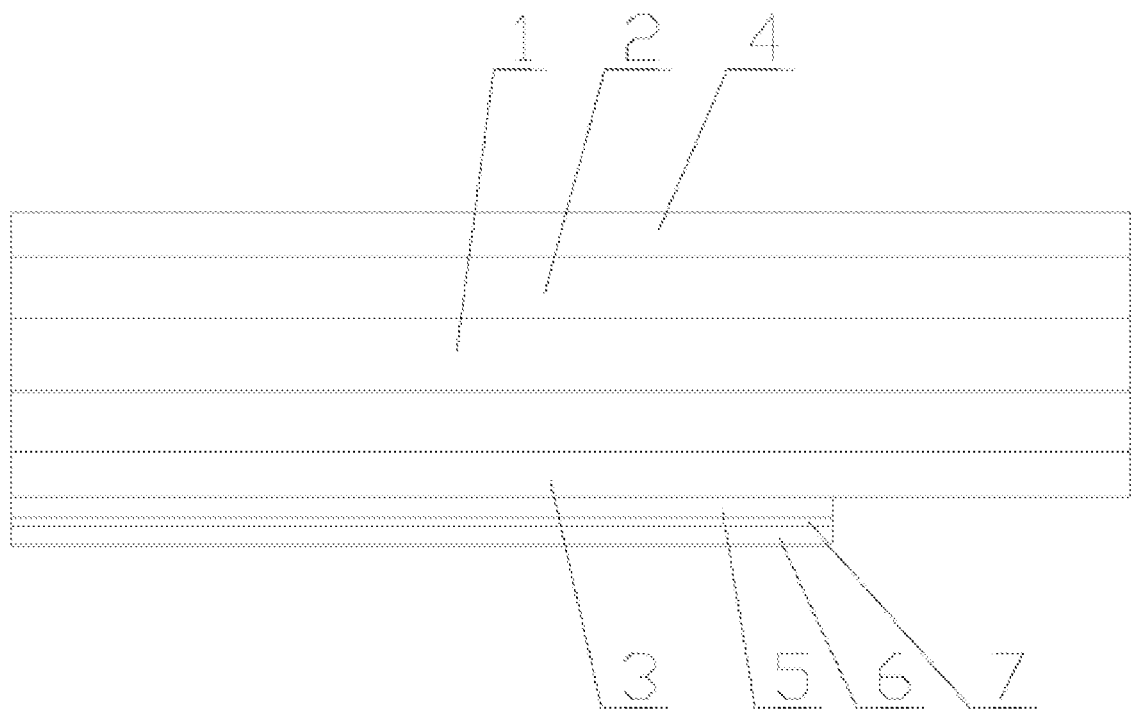
FIG. 2 is an overall structural diagram of embodiment 3 of the present invention.

In the drawings: 1. porous polymer membrane; 2. impermeable membrane; 3. first electrode; 4. second electrode; 5. enzyme layer; 6. enzyme protective layer; 7. immobilization agent layer.

DETAILED DESCRIPTION OF THE EMBODIMENTS

To make the object, technical solution, and advantages of the embodiment of the present invention clearer, the technical solution in the embodiment of the present invention is described clearly and completely in combination with the embodiment of the present invention. The described embodiment is a part of the embodiment of the present invention, but not the whole embodiment. All other embodiments obtained by those ordinarily skilled in the art based on the embodiments in the present invention without creative work shall fall within the scope of protection of the present invention.

Embodiment 1

Figure 3:
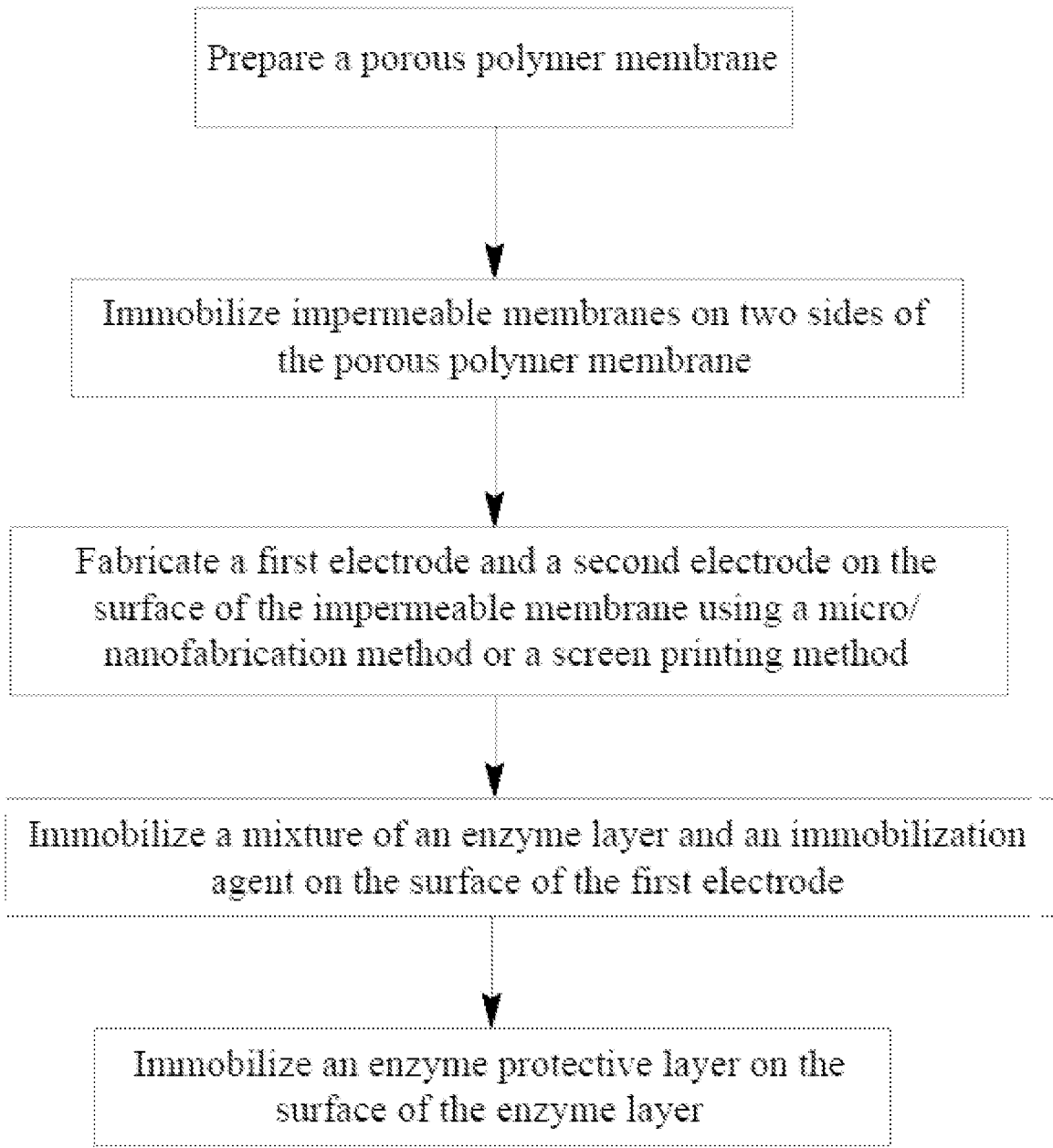
FIG. 3, FIG. 4, FIG. 5, FIG. 6 are flowcharts of embodiment 1 of the present invention.
Figure 4:
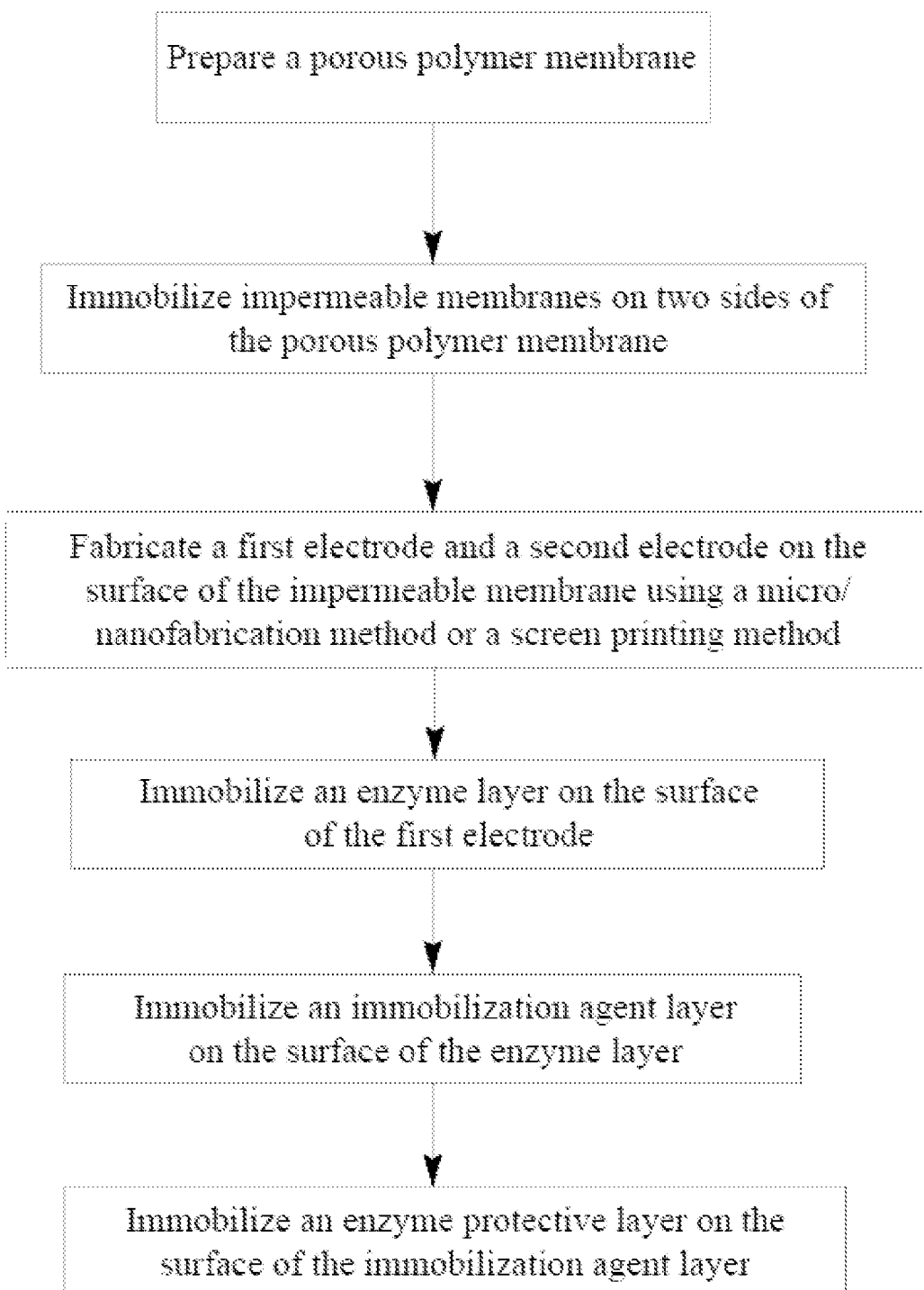
Figure 5:
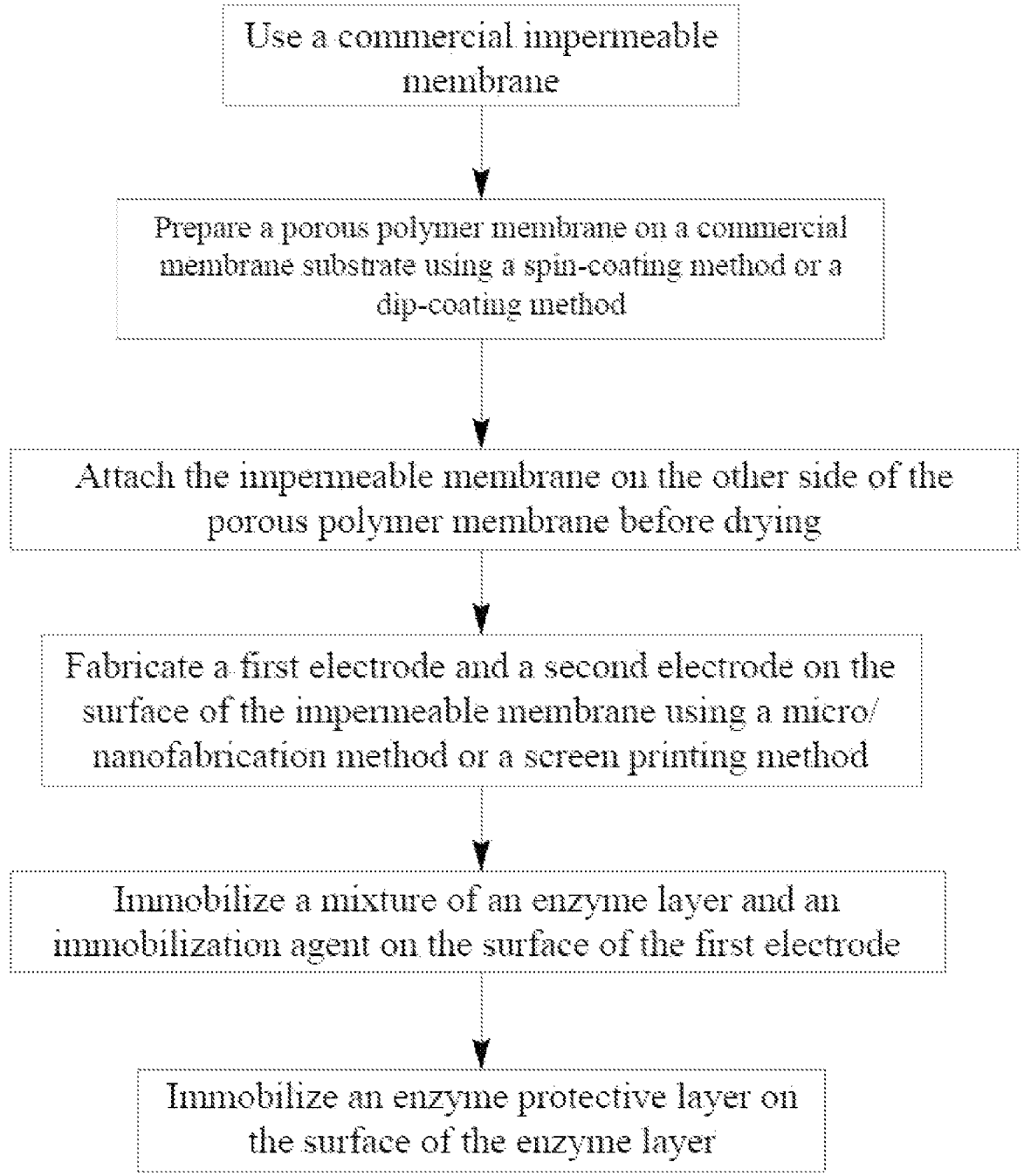

As shown in FIGS. 1, 3, and 5, the present embodiment discloses a diabetes biosensor, including a porous polymer membrane 1; two sides of the porous polymer membrane 1 are provided with impermeable membranes 2; the impermeable membrane 2 on one side is provided with a first electrode 3, the impermeable membrane 2 on the other side is provided with a second electrode 4; the surface of the first electrode 3 is provided with an enzyme layer 5, and the surface of the enzyme layer 5 is provided with an enzyme protective layer 6. The enzyme layer 5 is mixed with an immobilization agent on the surface of the first electrode 3. The immobilization agent is glutaraldehyde. The enzyme protective layer 6 is a polymer composite material or a multi-layer material, and the polymer composite material is one or more of polyvinyl alcohol, polyethylene glycol, and polyurethane.

In the present embodiment, the porous polymer membrane 1 is made of a mixture such as polyglycidyl methacrylate and polyethylene glycol, or a mesoporous polymer of polyvinyl alcohol, the porous polymer membrane 1 and the impermeable membrane 2 can both be prepared by a spin-coating method or a dip-coating method, and the impermeable membrane 2 may also be selected from commercially available products. A length of the porous polymer membrane 1 is 0.5 mm to 15 mm, a width of the porous polymer membrane 1 is 100 μm to 2 mm, and a thickness of the porous polymer membrane 1 is 100 μm to 1 mm.

The impermeable membrane 2 is made of Teflon, polypropylene, polyethylene, polyvinyl chloride, polyethylene terephthalate, polycarbonate, polyurethane, thermoplastic polyurethane, polyimide, glass fiber, silk fibroin, chitosan, polylactic acid, silica gel, rubber, latex, thermoplastic elastomer, or perfluoro ethylene-propylene copolymer, which has waterproof characteristics so that the porous polymer membrane, the impermeable membrane 2, the first electrode 3, and the second electrode 4 together constitute a sandwich sensor.

In particular, the impermeable membrane 2 is selected from a commercial membrane or self-made.

Figure 6:
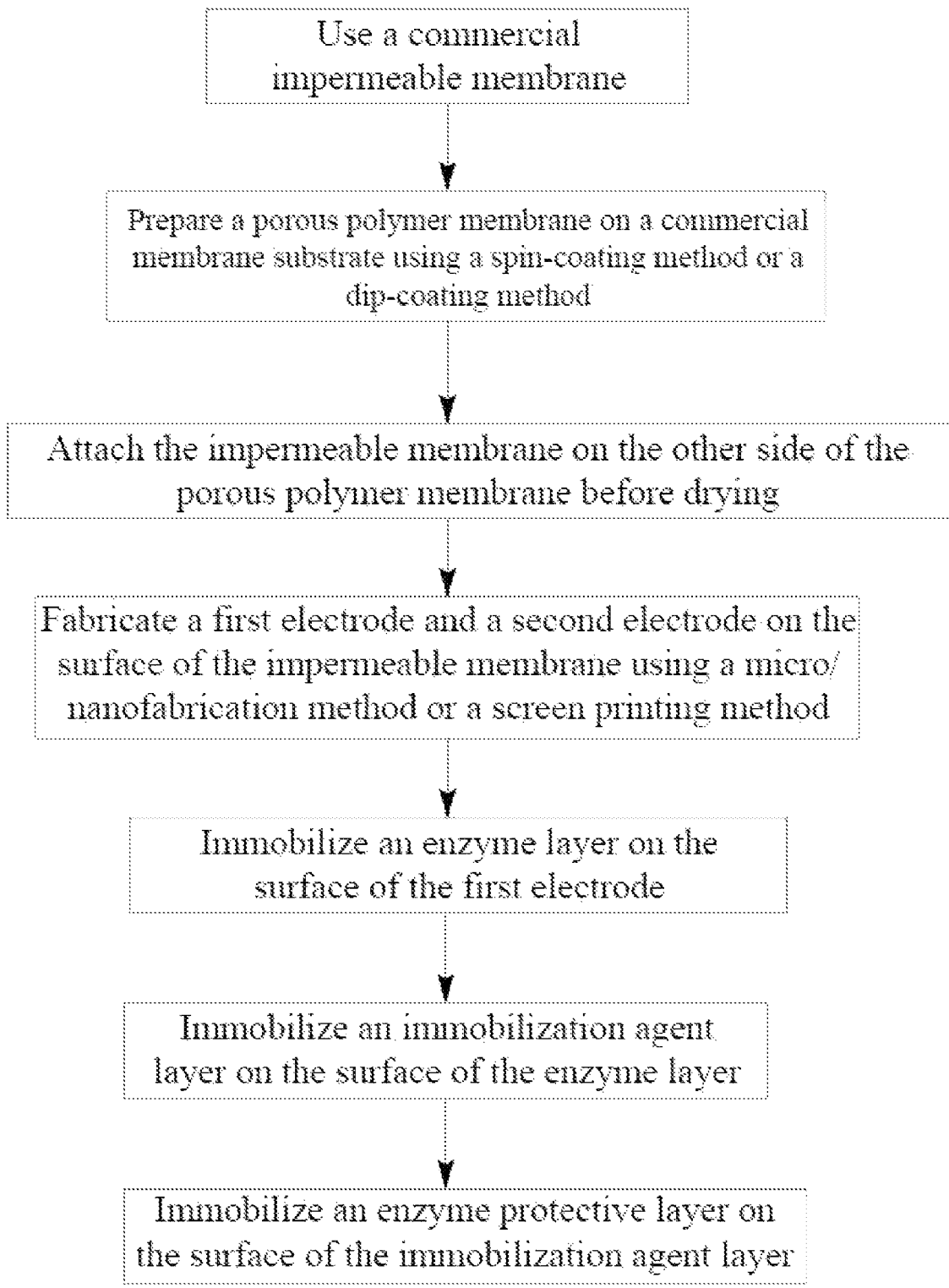

In FIGS. 5 and 6, when the impermeable membrane 2 is selected from the commercial membrane, the porous polymer membrane 1 is prepared by a spin-coating method or a dip-coating method on a commercial membrane substrate, and the impermeable membrane is attached to the other side of the porous polymer membrane 1 before drying.

When the impermeable membrane 2 is a self-made membrane, a first layer of impermeable membrane 2 is formed by spin-coating a polymer aqueous solution for preparing the impermeable membrane 2, followed by drying; and then another layer of impermeable membrane 2 polymer liquid is spin-coated, followed by drying, and then an enzyme layer 5 setting process is performed.

A method for preparing the enzyme layer 5 and an enzyme protective layer is as follows: dropping the enzyme layer 5 and the enzyme protective layer liquid on an electrode to cover an integral electrode, or spin-coating the enzyme layer 5 and the enzyme protective layer liquid to cover the integral electrode, or printing the enzyme layer 5 and the enzyme protective layer liquid on parts or the whole of the electrode.

The first electrode 3 is a working electrode, the second electrode 4 is a reference electrode/counter electrode, the second electrode 4 has the functions of both a reference electrode and a counter electrode and the first electrode 3 and the second electrode 4 together form a two-electrode system.

In the present embodiment, the two-electrode system is fabricated using a micro/nanofabrication method, including the following steps:
(1) working electrode: evaporation or sputtering of the micro/nanofabrication method is used to obtain a nanolayer of gold or platinum before electroplating thereon to produce a PB layer to obtain a gold/PB electrode or a platinum/PB electrode; and
(2) reference electrode/counter electrode: a silver electrode is produced through sputtering or evaporation, and then part of the silver in a ferric chloride solution generates silver chloride through a chemical reaction to obtain a silver/silver chloride electrode.

The first electrode 3 is made of a carbon composite material, a gold composite material, or a platinum composite material, and the second electrode 4 is made of silver/silver chloride.

The porous polymer membrane 1 has the feature of multiple pores to facilitate the penetration of drug liquid, and the impermeable membranes 2 on two sides of the porous polymer membrane 1 have the feature of impermeable; the porous polymer membrane 1, the impermeable membrane 2, the first electrode 3, and the second electrode 4 together constitute a sandwich sensor capable of detecting the glucose concentration in the subcutaneous tissue liquid. The glucose generates hydrogen peroxide under the action of glucose oxidase, and a constant voltage is applied on the working electrode (relative to the reference electrode/counter electrode); after the hydrogen peroxide generates electrons gain and loss on the working electrode, a current signal change on the working electrode is generated and detected by the circuit board or chip, thereby enabling the biosensor to perform rapid and continuous measurement on the blood glucose concentration. In addition, the biosensor can be used as a device for injecting medicine, which facilitates the use of the biosensor to inject insulin into a patient with a high blood glucose concentration to control the blood glucose level.

Embodiment 2

The present embodiment differs from embodiment 1 only in that the two-electrode system is fabricated using a screen printing method, and the steps are as follows:
(1) working electrode: a gold composite paste, a platinum composite paste, or a carbon composite paste is screen printed; and
(2) reference electrode/counter electrode: a silver/silver chloride composite paste is screen printed.

Embodiment 3

As shown in FIGS. 2, 4, 6, 8, and 10, the present embodiment differs from embodiment 1 only in that the enzyme layer 5 is directly added to the surface of the first electrode 3, an immobilization agent layer 7 is provided between the enzyme protective layer 6 and the enzyme layer 5, the enzyme protective layer 6 is a multi-layer material, and the multi-layer material is one or more of glutaraldehyde, polyvinyl alcohol, polyethylene glycol, and polyurethane.

Embodiment 4

The present embodiment, based on embodiment 1, discloses the application of a diabetes biosensor in other diseases, using this method to inject other diseases requiring the injection of pharmaceutical agents.

Embodiment 5

The present embodiment differs from embodiment 1 only in that the immobilization agent is selected from chitosan or Nafion.

Embodiment 6

In FIG. 7, the present embodiment discloses a method for fabricating a diabetes biosensor, including the following steps: fabricating a first electrode and a second electrode on the surface of the impermeable membrane using a micro/nanofabrication method or a screen printing method, followed by drying; preparing a porous polymer membrane using a spin-coating method or a dip-coating method, followed by drying; spin-coating another layer of impermeable membrane polymer liquid, followed by drying; immobilizing a mixture of an enzyme layer and an immobilization agent on the surface of the first electrode; and immobilizing an enzyme protective layer on the surface of the enzyme layer.

Embodiment 7

Figure 8:
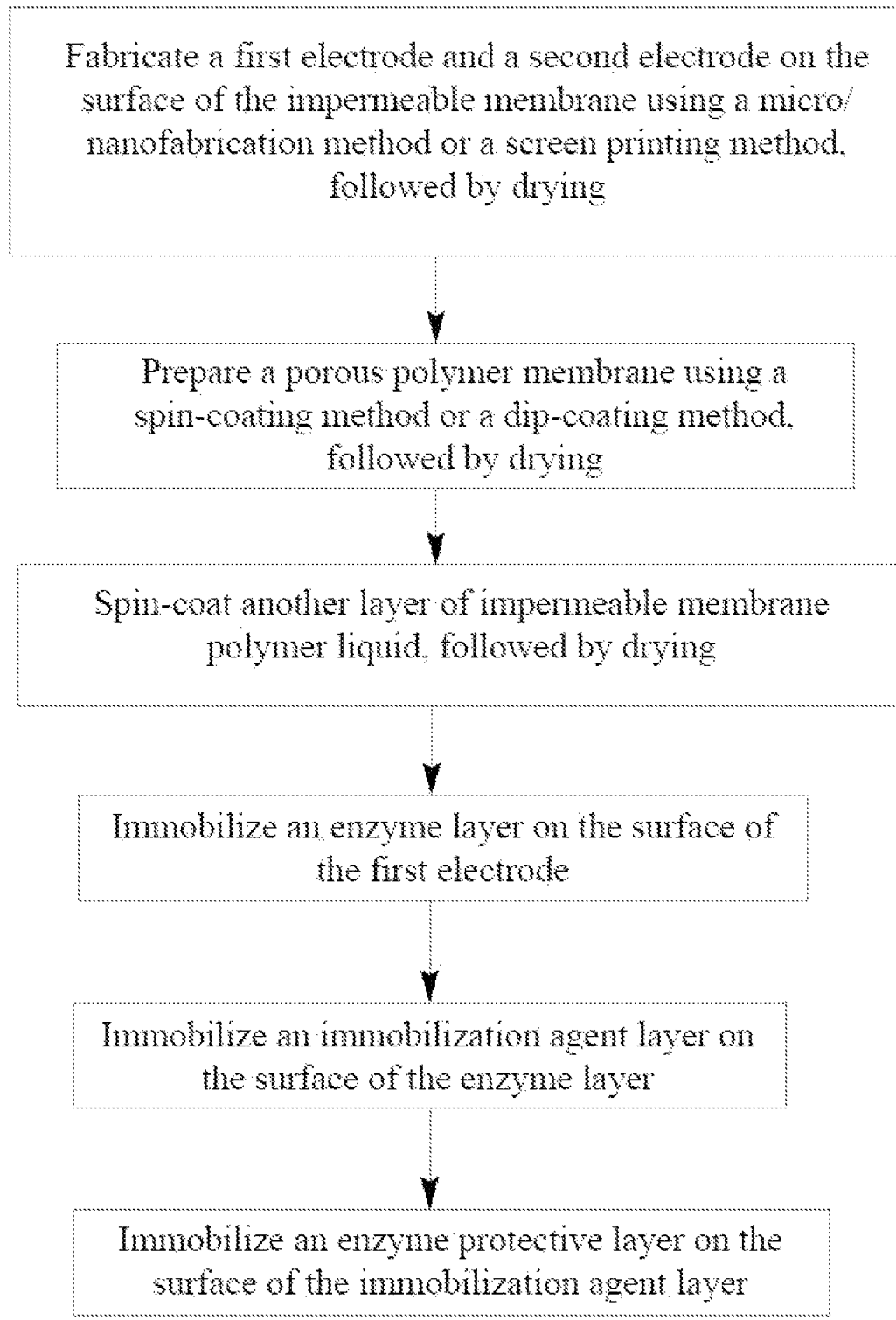
FIG. 8 is a flowchart of embodiment 7 of the present invention.

In FIG. 8, the present embodiment discloses a method for fabricating a diabetes biosensor, which differs from embodiment 6 only in that the last two steps are replaced by immobilizing an enzyme layer on the surface of the first electrode, immobilizing an immobilization agent layer on the surface of the enzyme layer, and immobilizing an enzyme protective layer on the surface of the immobilization agent layer.

Embodiment 8

Figure 9:
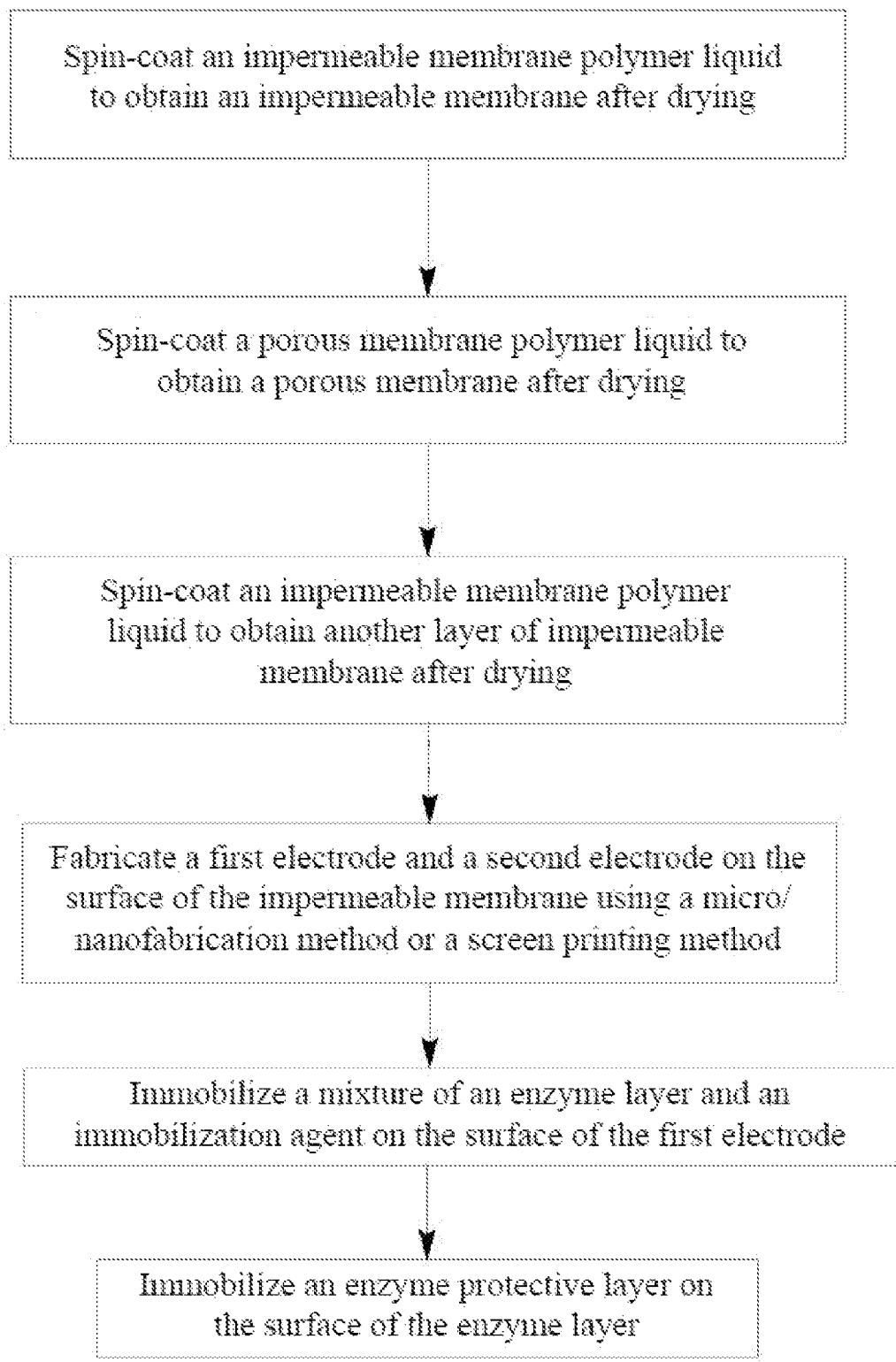
FIG. 9 is a flowchart of embodiment 8 of the present invention.

In FIG. 9, the present embodiment discloses a method for fabricating a diabetes biosensor, including the following steps: spin-coating an impermeable membrane polymer liquid to obtain an impermeable membrane after drying; spin-coating a porous membrane polymer liquid to obtain a porous membrane after drying; spin-coating an impermeable membrane polymer liquid to obtain another layer of impermeable membrane after drying; fabricating a first electrode and a second electrode on the surface of the impermeable membrane using a micro/nanofabrication method or a screen printing method; immobilizing a mixture of an enzyme layer and an immobilization agent on the surface of the first electrode; and immobilizing an enzyme protective layer on the surface of the enzyme layer.

Embodiment 9

Figure 10:
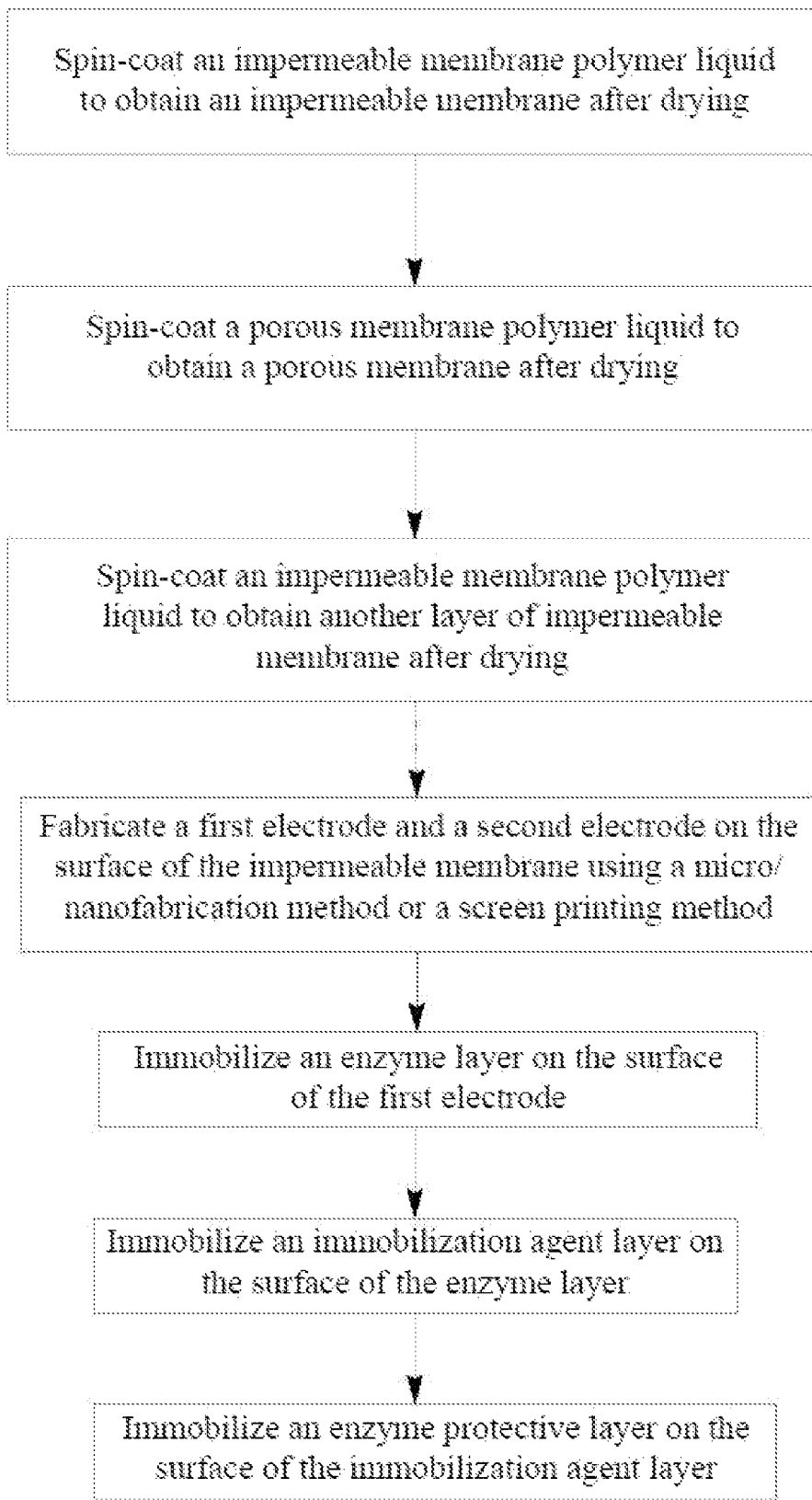
FIG. 10 is a flowchart of embodiment 9 of the present invention.

In FIG. 10, a method for fabricating a diabetes biosensor is disclosed, which differs from embodiment 8 only in that the last two steps are replaced by immobilizing an enzyme layer on the surface of the first electrode, immobilizing an immobilization agent layer on the surface of the enzyme layer, and immobilizing an enzyme protective layer on the surface of the immobilization agent layer.

The above embodiments are only used to illustrate the technical solutions of the present invention, not to limit them; although the present invention has been described in detail concerning the foregoing embodiments, the ordinarily skilled person in the art should understand that it is still possible to make modifications to the technical solutions documented in the foregoing embodiments or to make equivalent substitutions for some of the technical features therein; and such modifications or substitutions do not make the essence of the corresponding technical solutions deviate from the spirit and the scope of the technical solutions of the various embodiments of the present invention.

What is claimed is:

1. A diabetes biosensor, wherein the biosensor comprises:
a porous polymer membrane with a thickness of 100 μm to 1 mm;
two sides of the porous polymer membrane are provided with impermeable membranes, wherein the porous polymer membrane is made of a mesoporous polymer, wherein the mesoporous polymer is a mixture of polyglycidyl methacrylate and polyethylene glycol, or polyvinyl alcohol;
a first impermeable membrane on one side is provided with a first electrode, a second impermeable membrane on the other side is provided with a second electrode;
a surface of the first electrode is provided with an enzyme layer, and a surface of the enzyme layer is provided with an enzyme protective layer;
an immobilization agent layer is provided between the enzyme protective layer and the enzyme layer, wherein an immobilization agent on the enzyme layer is chitosan; and
the first and second impermeable membranes are selected from a commercial membrane or self-made.

2. The diabetes biosensor according to claim 1, wherein a length of the porous polymer membrane is 0.5 mm to 15 mm, and a width of the porous polymer membrane is 100 μm to 2 mm.

3. The diabetes biosensor according to claim 1, wherein the first electrode is a working electrode, the second electrode is a reference electrode/counter electrode, and the first electrode and the second electrode together form a two-electrode system;
the two-electrode system is fabricated using a micro/nanofabrication method or a screen printing method;
the micro/nanofabrication method of the two-electrode system is as follows:
(1) working electrode: evaporation or sputtering of the micro/nanofabrication method is used to obtain a nano-layer of gold or platinum before electroplating thereon to produce a Prussian Blue (PB) layer to obtain a gold/PB electrode or a platinum/PB electrode; and
(2) reference electrode/counter electrode: a silver electrode is produced through sputtering or evaporation, and then part of the silver in a ferric chloride solution generates silver chloride through a chemical reaction to obtain a silver/silver chloride electrode; and
the screen printing method of the two-electrode system is as follows:
(1) working electrode: a gold composite paste, a platinum composite paste, or a carbon composite paste is screen printed; and
(2) reference electrode/counter electrode: a silver/silver chloride composite paste is screen printed.

4. The diabetes biosensor according to claim 3, wherein the first electrode is made of a carbon composite material, a gold composite material, or a platinum composite material, and the second electrode is made of silver/silver chloride.

5. The diabetes biosensor according to claim 3, wherein:
the enzyme layer is immobilized on the surface of the first electrode with the immobilization agent, and the immobilization agent is chitosan; and
the enzyme protective layer is a polymer composite material or a multi-layer material, and the polymer composite material is one or more of polyvinyl alcohol, polyethylene glycol, and polyurethane.

6. The diabetes biosensor according to claim 3, wherein:
the enzyme layer is directly added to the surface of the first electrode; and
the enzyme protective layer is a multi-layer material, and the multi-layer material is one or more of glutaraldehyde, polyvinyl alcohol, polyethylene glycol, and polyurethane.

7. The diabetes biosensor according to claim 1, wherein:
when the impermeable membranes are selected from the commercial membrane, the porous polymer membrane is prepared by a spin-coating method or a dip-coating method on a commercial membrane substrate, and the impermeable membranes are attached to the other side of the porous polymer membrane before drying; and
when the impermeable membranes are the self-made membrane, a first layer of the impermeable membranes are formed by spin-coating a polymer aqueous solution for preparing the impermeable membrane, followed by drying; and then another layer of impermeable membrane polymer liquid is spin-coated, followed by drying, and then an enzyme layer setting process is performed.

8. The diabetes biosensor according to claim 1, wherein the impermeable membranes are made of Teflon (polytetrafluoroethylene), polypropylene, polyethylene, polyvinyl chloride, polyethylene terephthalate, polycarbonate, polyurethane, thermoplastic polyurethane, polyimide, glass fiber, silk fibroin, chitosan, polylactic acid, silica gel, rubber, latex, thermoplastic elastomer, or perfluoro ethylene-propylene copolymer.

9. A method for preparing the enzyme layer and the enzyme protective layer according to claim 1, the method comprising:
dropping the enzyme layer and the enzyme protective layer liquid on the first electrode to cover an integral electrode, or spin-coating the enzyme layer and the enzyme protective layer liquid to cover the integral electrode, or printing the enzyme layer and the enzyme protective layer liquid on parts or the whole of the first electrode.

* * * * *